United States Patent
Chen

(10) Patent No.: US 11,555,812 B2
(45) Date of Patent: Jan. 17, 2023

(54) METHODS OF DETERMINING CATION EXCHANGE SITES OCCUPIED BY CRUDE OIL AND THE WETTABILITY OF CATION EXCHANGE SITES IN ROCK CORE SAMPLES IN A NON-PRESERVED STATE

(71) Applicant: SAUDI ARABIAN OIL COMPANY, Dhahran (SA)

(72) Inventor: Quan Chen, Al Khobar (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 269 days.

(21) Appl. No.: 16/859,163

(22) Filed: Apr. 27, 2020

(65) Prior Publication Data

US 2021/0333258 A1  Oct. 28, 2021

(51) Int. Cl.
| | |
|---|---|
| *G01N 33/24* | (2006.01) |
| *E21B 43/20* | (2006.01) |
| *E21B 49/00* | (2006.01) |
| *G01N 13/00* | (2006.01) |

(52) U.S. Cl.
CPC .............. *G01N 33/24* (2013.01); *E21B 43/20* (2013.01); *E21B 49/00* (2013.01); *G01N 13/00* (2013.01)

(58) Field of Classification Search
CPC ...... G01N 33/24; G01N 13/00; G01N 15/082; E21B 43/20; E21B 49/00; E21B 49/02
See application file for complete search history.

(56) References Cited

U.S. PATENT DOCUMENTS

| | | |
|---|---|---|
| 4,790,180 A | 12/1988 | Sinnokrot |
| 5,858,791 A | 1/1999 | Lemaire |
| 7,896,080 B1 | 3/2011 | Watters et al. |
| (Continued) | | |

FOREIGN PATENT DOCUMENTS

GB  2238488 A  6/1991

OTHER PUBLICATIONS

S. P. Austin et al: "The measurement of the cation exchange capacity of core plugs by a nondestructive 'wet' chemical method", Advances in Core Evaluation IIa Reservoir Appraisal, 1991, pp. 293-308 (16 pages).

(Continued)

*Primary Examiner* — Benjamin R Schmitt
(74) *Attorney, Agent, or Firm* — Osha Bergman Watanabe & Burton LLP

(57) ABSTRACT

A method for determining properties of different cation exchange sites in a rock core sample at a non-preserved state may include displacing all native components out of the rock core sample before subjecting the rock core sample to coreflooding steps to determine a total amount of exchangeable cations adsorbed onto the cation exchange sites; injecting formation brine and then a reservoir crude oil into the rock core sample such that the rock core sample includes indigenous exchangeable cations adsorbed onto the cation exchange sites, cation exchange sites occupied by a crude oil, and one or more fluids; subjecting the rock core sample to coreflooding steps to displace the indigenous exchangeable cations, the crude oil, and the one or more fluids; determining an amount of indigenous exchangeable cations adsorbed onto the cation exchange sites; and determining at least one property of different cation exchange sites.

20 Claims, 5 Drawing Sheets

(56) References Cited

U.S. PATENT DOCUMENTS

| | | |
|---|---|---|
| 2012/0085555 A1 | 4/2012 | Collins et al. |
| 2012/0241149 A1 | 9/2012 | Chen et al. |
| 2017/0058186 A1 | 3/2017 | Oghena et al. |
| 2018/0291256 A1 | 10/2018 | Alwattari et al. |
| 2019/0094120 A1 | 3/2019 | Gmira et al. |
| 2021/0318259 A1* | 10/2021 | Stokes ................. G01N 27/221 |
| 2021/0333188 A1* | 10/2021 | Chen ...................... G01N 13/00 |
| 2021/0333191 A1* | 10/2021 | Chen ................... G01N 33/241 |

OTHER PUBLICATIONS

Colin Mcphee et al: "Core Sample Preparation" In: "Core Analysis—A Best Practice Guide; In: Developments in petroleum science; ISSN 0375-7361", Dec. 9, 2015 (Dec. 9, 2015), Elsevier, NL, pp. 135-179 (45 pages).

Kazak E S et al: "An ion-salt complex of rocks from the Bazhenov formation of West Sibera", Moscow University Geology Bulletin, Allerton Press, Heidelberg, vol. 72, No. 5, Dec. 23, 2017 (Dec. 23, 2017), pp. 368-375 (8 Pages).

Donald Hill: "Clay Stabilization—Criteria for Best Performance", Proceedings of SPE Formation Damage Control Symposium, 1982, pp. 127-138 (12 pages).

International Search Report and Written Opinion issued in International Application No. PCT/US2020/031410, dated Feb. 26, 2021 (16 pages).

\* cited by examiner

METHODS OF DETERMINING CATION EXCHANGE SITES OCCUPIED BY CRUDE OIL AND THE WETTABILITY OF CATION EXCHANGE SITES IN ROCK CORE SAMPLES IN A NON-PRESERVED STATE

BACKGROUND

A common practice in the oil and gas industry is to inject water into a hydrocarbon reservoir to maintain its pressure and displace hydrocarbons to production wells. This injection of water is commonly referred to as secondary stage injection or secondary recovery. Seawater and aquifer water are some of the more widely used resources for injection. Injection of a second fluid in order to displace additional hydrocarbons after no more hydrocarbons are being extracted using the first fluid is referred to as tertiary stage injection or tertiary recovery. A remaining portion of the initial hydrocarbons in the reservoir can be extracted utilizing expensive enhanced recovery techniques, such as carbon dioxide ($CO_2$) injection or chemical flooding. A relatively more recent technique involves injection of aqueous solutions with modified ionic compositions.

Understanding properties of the hydrocarbon reservoir can assist in optimizing extraction of the stored hydrocarbons from the reservoir. One technique to understand properties of the hydrocarbon reservoir is to develop computer-generated software models of all or portions of the reservoir. To develop such models, a reservoir rock sample from the hydrocarbon reservoir is evaluated and results of the evaluation are provided as an input to the computer software program that generates the software models. The reservoir rock sample can be evaluated by performing one or more of several experiments under laboratory conditions or under reservoir conditions (that is, the conditions experienced by the sample in the hydrocarbon reservoir). Rock wettability, specifically, the wettability of the porous structure within the rock, is one of the parameters of the reservoir rock sample that can be evaluated.

Wettability is the tendency of a fluid to spread across or adhere to a solid surface in the presence of other immiscible fluids. Wettability can describe the preference of a solid to be in contact with one fluid rather than another. In relation to the oil and gas industry, wettability can refer to the interaction between fluids such as hydrocarbons or water and a reservoir rock. The wettability of a reservoir can affect the hydrocarbon extraction process. Because wettability can influence not only the profile of initial hydrocarbon saturation but also the hydrocarbon extraction process, such as water flooding and enhanced oil recovery (EOR) processes. However, conventional wettability measurement methods cannot determine the wettability of different cation exchange sites.

Further, existence of clay in reservoir formations has a great impact on reservoir quality of sandstone facies. Clay minerals have different effects on the characteristics of oil reservoirs such as reduction of effective porosity and permeability or overestimation of water saturation due to the increased conductivity. In addition, the presence of clay causes the instability of some parts of wellbore wall. For these reasons, the study of clays in petroleum related investigations is so vital. Cation exchange capacity (CEC) is one of the parameters that is useful for identifying clays and their physical and chemical properties.

The CEC of a rock sample is often determined by a wet chemistry method. However, the determined cation exchange capacity by a wet chemistry method is not reservoir representative for the following reasons: (1) the rock sample is cleaned to remove any oil in the rock sample, which is not representative of the in-situ reservoir conditions; (2) the rock sample is ground to fine particles. However, excessive grinding will increase the cation exchange capacity by exposing more cation exchange sites than the case at the in-situ reservoir conditions, resulting in the overestimation cation exchange capacity. On the other hand, insufficient grinding will lead to some reservoir representative cation exchange sites not being exposed, resulting in underestimation of the cation exchange capacity; and (3) the determined cation exchange capacity does not identity any reservoir representative exchangeable cations on the exchange sites and which of the sites are occupied by crude oil. Oil adsorbed onto the cation exchange sites may impact the cation exchange capacity. Cation exchange between a rock surface and a brine being flushed therethrough can desorb oil that is adsorbed to the surface, thereby impacting oil recovery efforts from the reservoir.

Accordingly, there exists a continuing need for developments in rock sample analysis to improve the enhanced oil recovery efforts.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method for determining properties of different cation exchange sites in a rock core sample, at a non-preserved state of the rock core sample includes providing a rock core sample in a non-preserved state; displacing all native components out of the rock core sample; subjecting the rock core sample clean of native components to a plurality of coreflooding steps to determine a total amount of exchangeable cations adsorbed onto the cation exchange sites when the rock core sample is clean of native components; injecting formation brine and then a reservoir crude oil into the rock core sample until reaching irreducible water saturation and equilibrium between formation brine, the reservoir crude oil, and the cation exchange sites, such that rock core sample includes a plurality of indigenous exchangeable cations adsorbed onto the cation exchange sites, a plurality of cation exchange sites occupied by a crude oil, and one or more fluids occupying pore spaces in the rock core sample; subjecting the rock core sample to a plurality of coreflooding steps, the plurality of coreflooding step displacing the plurality of indigenous exchangeable cations, the crude oil, and the one or more fluids in at least two separate coreflooding steps to render the rock core sample clean of the indigenous cations; determining an amount of indigenous exchangeable cations adsorbed onto the cation exchange sites; and determining at least one property of different cation exchange sites in the rock core sample based on the amount of indigenous exchangeable cations and the total amount of exchangeable cations.

In another aspect, embodiments disclosed herein relate to a method for determining an amount of different cation exchange sites occupied by crude oil in a rock core sample, at a non-preserved state of the rock core sample that includes providing a rock core sample in a non-preserved state; displacing all native components out of the pore space of the rock core sample by alternately injecting a first organic solvent and a second organic solvent, wherein the second organic solvent is the last injected; displacing the second organic solvent with a formation brine to adsorb a plurality of exchangeable cations onto the different cation exchange sites of the rock core sample; displacing an excess of cations from the formation brine present in a plurality of interstitial pore spaces of the rock core sample by using a third organic solvent; displacing the plurality of exchangeable cations adsorbed onto the different cation exchange sites of the rock core sample with a first injection fluid until completion of extraction; displacing the first injection fluid with the formation brine such that the cations present in the formation brine adsorb onto the cation exchange sites; injecting a reservoir crude oil into the rock core sample until reaching irreducible water saturation and equilibrium between formation brine, the reservoir crude oil, and the cation exchange sites, such that rock core sample includes a plurality of indigenous exchangeable cations adsorbed onto the cation exchange sites, a plurality of cation exchange sites occupied by a crude oil, and one or more fluids occupying pore spaces in the rock core sample; displacing the reservoir crude oil in the rock core sample with formation brine until oil ceases production; displacing an excess of cations present in a plurality of interstitial pore spaces of the rock core sample by using a fourth organic solvent; displacing the plurality of indigenous cations adsorbed onto the cation exchange sites of the rock core sample with a second injection fluid until completion of extraction; calculating an amount of indigenous exchangeable cations adsorbed onto the cation exchange sites and a total amount of the exchangeable cations adsorbed onto the cation exchange sites; and calculating the amount of the different cation exchange sites occupied by crude oil based on the amount of indigenous exchangeable cations adsorbed onto the cation exchange sites and the total amount of the exchangeable cations adsorbed onto the cation exchange sites.

In yet another aspect, embodiments disclosed herein relate to a method for determining a wettability of different cation exchange sites of a rock sample, at a non-preserved state of the rock core sample that includes providing a rock core sample in a non-preserved state; displacing all native components out of the pore space of the rock core sample by alternately injecting a first organic solvent and a second organic solvent, wherein the second organic solvent is the last injected; displacing the second organic solvent with a formation brine to adsorb a plurality of exchangeable cations onto the different cation exchange sites of the rock core sample; displacing an excess of cations from the formation brine present in a plurality of interstitial pore spaces of the rock core sample by using a third organic solvent; displacing the plurality of exchangeable cations adsorbed onto the different cation exchange sites of the rock core sample with a first injection fluid until completion of extraction; displacing the first injection fluid with the formation brine such that the cations present in the formation brine adsorb onto the cation exchange sites; injecting a reservoir crude oil into the rock core sample until reaching irreducible water saturation and equilibrium between formation brine, the reservoir crude oil, and the cation exchange sites, such that rock core sample includes a plurality of indigenous exchangeable cations adsorbed onto the cation exchange sites, a plurality of cation exchange sites occupied by a crude oil, and one or more fluids occupying pore spaces in the rock core sample; displacing the reservoir crude oil in the rock core sample with formation brine until oil ceases production; displacing an excess of cations present in a plurality of interstitial pore spaces of the rock core sample by using a fourth organic solvent; displacing the plurality of indigenous cations adsorbed onto the cation exchange sites of the rock core sample with a second injection fluid until completion of extraction; calculating an amount of indigenous exchangeable cations adsorbed onto the cation exchange sites and a total amount of the exchangeable cations adsorbed onto the cation exchange sites; and calculating the wettability of the different cation exchange sites based on the amount of indigenous exchangeable cations adsorbed onto the cation exchange sites and the total amount of the exchangeable cations adsorbed onto the cation exchange sites.

Other aspects and advantages of the claimed subject matter will be apparent from the following description and the appended claims.

DETAILED DESCRIPTION

Figure 1:
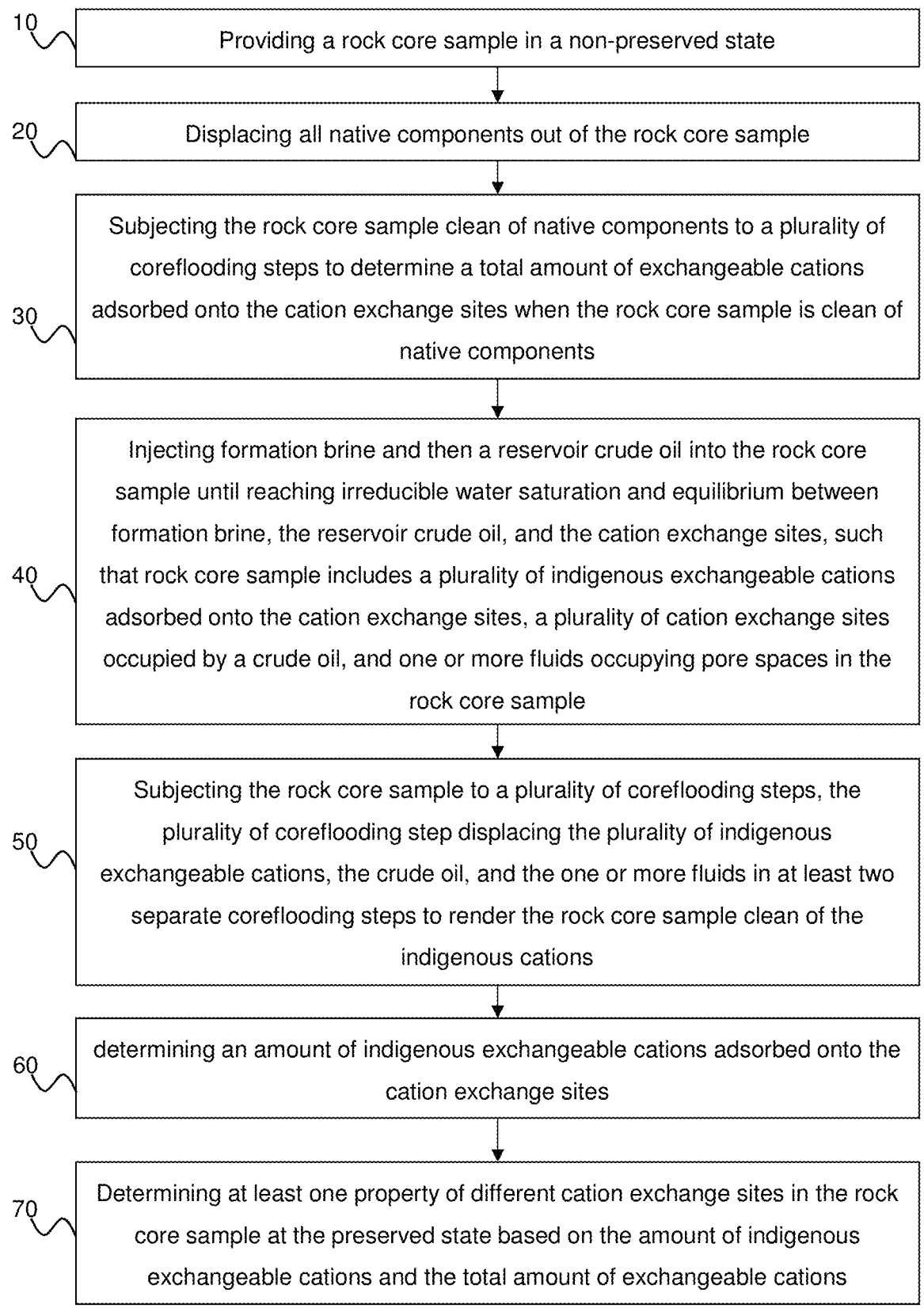
FIG. 1 shows a flow chart according to one or more embodiments of the present disclosure.

In one aspect, embodiments disclosed herein relate to methods of rock sample analysis to provide determinations concerning different cation exchange sites present in the rock core samples. Clay minerals in a reservoir or rock sample have negatively charged sites ($X^-$) on their surfaces which adsorb and hold cations (e.g., $Ca^{2+}$, $Mg^{2+}$, $Na^+$, and $K^+$) by electrostatic force. In particular, the present methods are directed to methodologies that allow for determinations concerning the wettability of different cation exchange sites in a rock core sample and/or different cation exchange site occupied by crude oil, when the rock is in a non-preserved state (i.e. not in the original reservoir condition).

Conventional methods of rock core analysis do not provide for distinctions based on different cation exchange sites, i.e., differentiating between $Ca^{2+}$, $Mg^{2+}$, $Na^+$, and $K^+$, for example. Moreover, conventionally, such testing should occur on a rock in preserved states. However, in accordance with embodiments of the present disclosure, a rock core sample in a non-preserved state may be subjected to a series of coreflood steps to provide such differentiation and in particular the wettability of the different sites and which of the different sites are occupied by crude oil. This may advantageously allow for enhanced oil recovery operations to be designed based on such different cation exchange sites and the properties thereof to result in greater efficacy in EOR operations. In particular, such determinations may be made by considering the indigenous exchangeable cations of $Na^+$, $K^+$, $Ca^{2+}$ and $Mg^{2+}$ adsorbed onto cation exchange sites ($[NaX]_e$, $[KX]_e$, $[CaX_2]_e$ and $[MgX_2]_e$) and the total exchangeable cations of $Na^+$, $K^+$, $Ca^{2+}$ and $Mg^{2+}$ adsorbed onto the cation exchange sites, ($[NaX]_T$, $[KX]_T$, $[CaX_2]_T$ and $[MgX_2]_T$). As used herein, the total exchangeable cations adsorbed onto the cation exchange sites refers to when all cation exchange sites are occupied by cations, whereas the indigenous exchangeable cations adsorbed onto the cation exchange sites in the native state in the reservoir. For example, depending on the wettability of the rock surface and the cation exchange sites, in particular, and whether the sites are oil-wet or water-wet, for example, some of the site may be occupied by crude oil, rather than cations. The present methods may determine the wettability of each exchange site and/or the amount of each site occupied by crude oil, for a rock sample that is not in a preserved state. As used herein, when the rock is in a preserved state, it, and specifically the cation exchange sites, is in the original reservoir condition, whereas a non-preserved state is not in the original reservoir condition.

As described herein, the present methodology uses coreflooding to sequentially displace native components out of the rock core sample and inject (and displace) replacement fluids therethrough during the analysis. In particular, because the rock sample is not in a preserved state, the present methods displace all native components therefrom. Once the pore space of the rock core sample is entirely cleaned of all native components, the rock core sample may be filled with formation brine having cations (of the indigenous type) in order to obtain data concerning the total exchangeable sites (which may be only partially occupied by indigenous cations in the reservoir). Then, reservoir crude oil may be injected into the rock sample until reaching irreducible water saturation and equilibrium to replicate the rock sample in a native state. Then, the present method may separately displace excess components such as fluids (including excess cations) from the pore spaces, then indigenous cations from exchange sites (by replacing the indigenous cations with replacement cations). Both the indigenous adsorbed cations and the "total" adsorbed cations may be quantified and compared in order to determine the wettability of each exchange site and/or the amount of each site occupied by crude oil.

Such a coreflooding system may include a coreholder, a pumping system, an effluent collection system, a measurement system, as well as temperature and pressure control so that coreflooding experiments may be conducted at conditions mimicking reservoir conditions. Such systems are commercially available. Coreflooding may be utilized on rock types having a permeability of at least 0.1 millidarcy.

Referring now to FIG. 1, a flow chart according to one or more embodiments is shown. As shown, stage 10 may include providing a rock core sample in a non-preserved state. Stage 20 may include displacing all native components out of the rock core sample. Stage 30 may include subjecting the rock core sample clean of native components to a plurality of coreflooding steps to determine a total amount of exchangeable cations adsorbed onto the cation exchange sites when the rock core sample is clean of native components. State 40 may include injecting formation brine and then a reservoir crude oil into the rock core sample until reaching irreducible water saturation and equilibrium between formation brine, the reservoir crude oil, and the cation exchange sites, such that rock core sample includes a plurality of indigenous exchangeable cations adsorbed onto the cation exchange sites, a plurality of cation exchange sites occupied by a crude oil, and one or more fluids occupying pore spaces in the rock core sample. Stage 50 may include subjecting the rock core sample to a plurality of coreflooding steps, the plurality of coreflooding step displacing the plurality of indigenous exchangeable cations, the crude oil, and the one or more fluids in at least two separate coreflooding steps to render the rock core sample clean of the indigenous cations. Stage 60 may include determining an amount of indigenous exchangeable cations adsorbed onto the cation exchange sites. Stage 70 may include determining at least one property of different cation exchange sites in the rock core sample based on the amount of indigenous exchangeable cations and the total amount of exchangeable cations.

Figure 2:
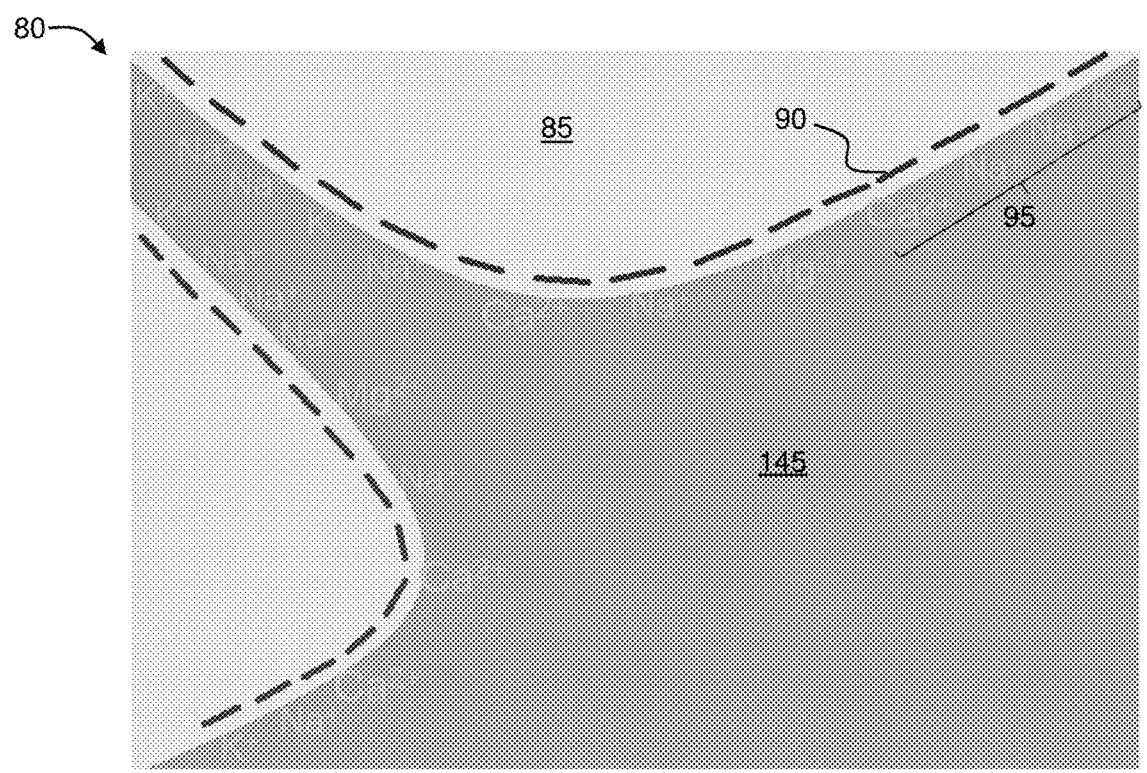
FIGS. 2-9 show schematics of a rock core sample during sequential coreflooding operations in accordance with one or more embodiments of the present disclosure.

FIGS. 2-9 illustrate schematics of a rock core sample 80 during progressive stages of the present coreflooding operations. Initially, the rock core sample 80 in the non-preserved state (i.e., not at original reservoir conditions) has a plurality of rock particles 85. The rock particles have exchange sites 90 present on the surface thereof. While there may be exchangeable cations 95 adsorbed to the exchange sites, because the rock core sample 80 is a non-preserved stated, the exchangeable cations 90 may not be used in determining the properties of the exchange sites. Thus, the rock core sample is coreflooded with an alternating sequence of a plurality of organic solvents. Such organic solvents may include at least one solvent that may be effective to remove any residual oil present in the rock core sample 80, including oil adsorbed to the exchange sites 90 as well as residual oil present in the pore spaces between rock particles. The effect of such coreflooding is shown in FIG. 2. Additionally, the organic solvents may also include at least one solvent that is effective to remove water and salts from the pore space of the rock core sample 80. In one or more embodiments, one solvent may be toluene and the other may be methanol. It is envisioned that the solvent miscible in water (e.g., methanol) may be the last organic solvent injected into the rock core sample 80 (such that the water-miscible organic solvent can be completely displaced out of the rock core sample by formation brine as described in the following paragraph). As shown in FIG. 2, the rock core sample 80, after alternating injection of organic solvents, may have the exchangeable cations 95 adsorbed to the exchange sites 90, with the pore space being occupied entirely by the water-miscible organic solvent 145.

Figure 3:
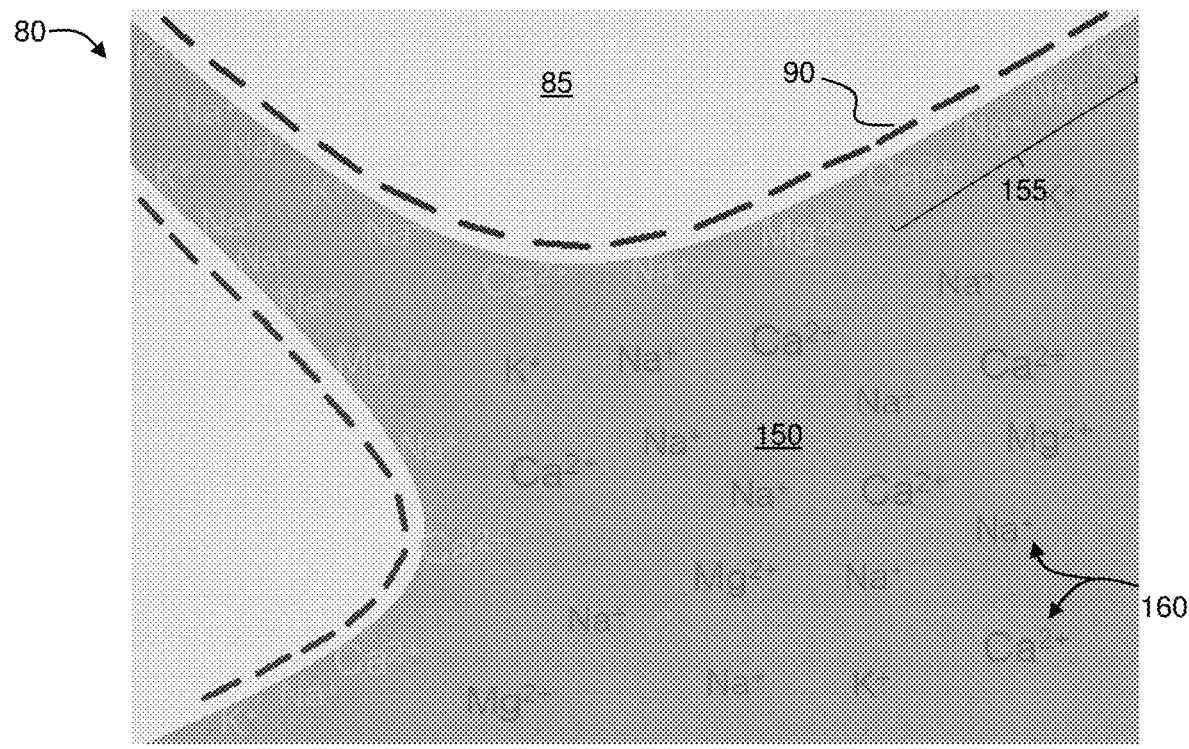

Following the alternating solvent injection, the effect of which is illustrated in FIG. 2, a formation brine may be coreflooded into the rock core sample 80 to displace the water-miscible organic solvent 145 from the rock sample core 80. As shown in FIG. 3, following such displacement, formation brine 150 may be present in the pore spaces between rock particles 85. Formation brine 150 is injected in sufficient volume for complete displacement of organic solvent (145 in FIG. 2). Cations in formation brine exchange with exchangeable cations 95 such that exchangeable cations 155 are adsorbed to all exchange sites 90 present on the surface of rock particles 85. Because exchangeable cations 155 are adsorbed to all exchange sites 90, exchangeable cations 155 are referred to herein as "total" exchangeable cations 155. Excess cations 160 in formation brine 150 are also present in the pore spaces between rock particles 85. In order to have complete displacement and equilibrium of the exchange sites 90, a large volume of formation brine 150 may be used, for example, ranging from an estimated 50 to 80 pore volumes. For the purpose of estimating the volume of formation brine or other fluid that may be used for the coreflooding, the pore volume may be estimated by measuring the length and diameter and assuming a porosity of 30% for the rock core sample.

In one or more embodiments, the pore volume of the rock core sample 80 may be determined by NMR. Preferably, this determination may be performed as the rock core sample 80 is in a state illustrated in FIG. 3, as the rock core sample 80 contains a single fluid type therein, which may allow for fewer complexities in the NMR determination. The pore volume may be used to quantify the amount of cations relative to the pore volume of the rock core sample 80. However, a NMR analysis performed at another time may account for the presence of more than one fluid, such as a brine and oil.

Figure 4:
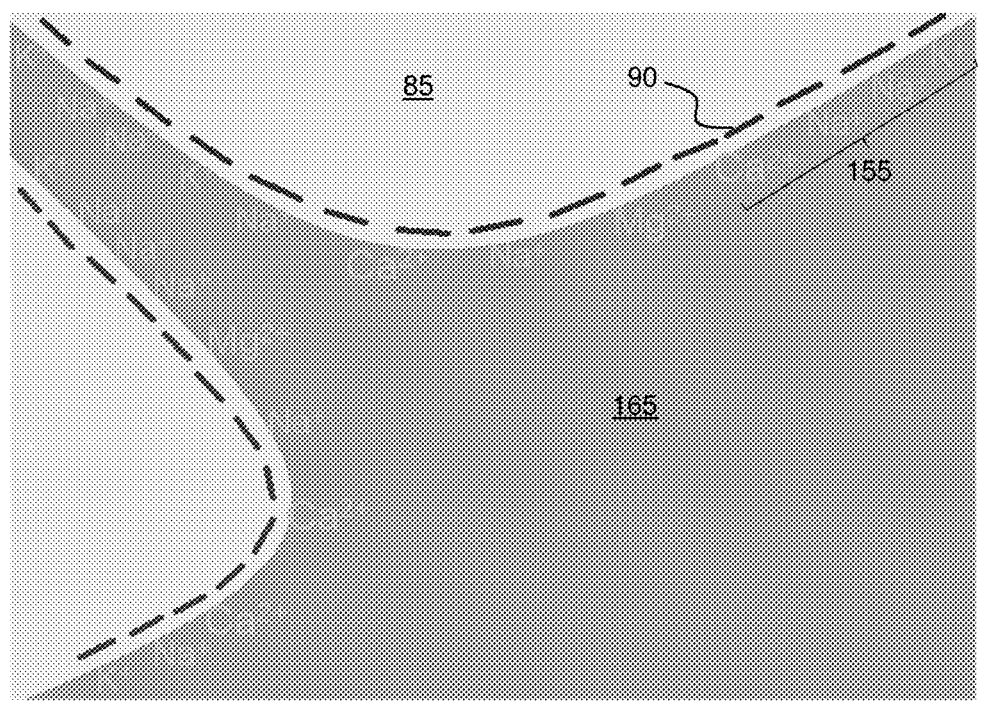

After equilibrating the exchange sites 90 with cations 155, the result of which is shown in FIG. 3, the excess cations 160 may be removed from the rock core sample 80. As shown in FIG. 4, excess cations and formation brine (160 and 150, respectively, in FIG. 3) may be displaced from the pore spaces between rock particles 85 by coreflooding the rock sample 80 with an organic solvent, such as but not limited 95% ethanol, to displace the excess cations 160 (shown in FIG. 3) from the rock core sample 80. To complete the displacement of excess cations 160, a large volume of organic solvent may be used, for example, ranging from 50 to 80 pore volumes. The effect of such displacement is shown in the schematic illustrated in FIG. 4. As shown in FIG. 4, while the exchange sites 90 still have the "total" exchangeable cations 155 adsorbed thereto, the pore space between the rock particles 85 is now occupied by organic solvent 165.

Figure 5:
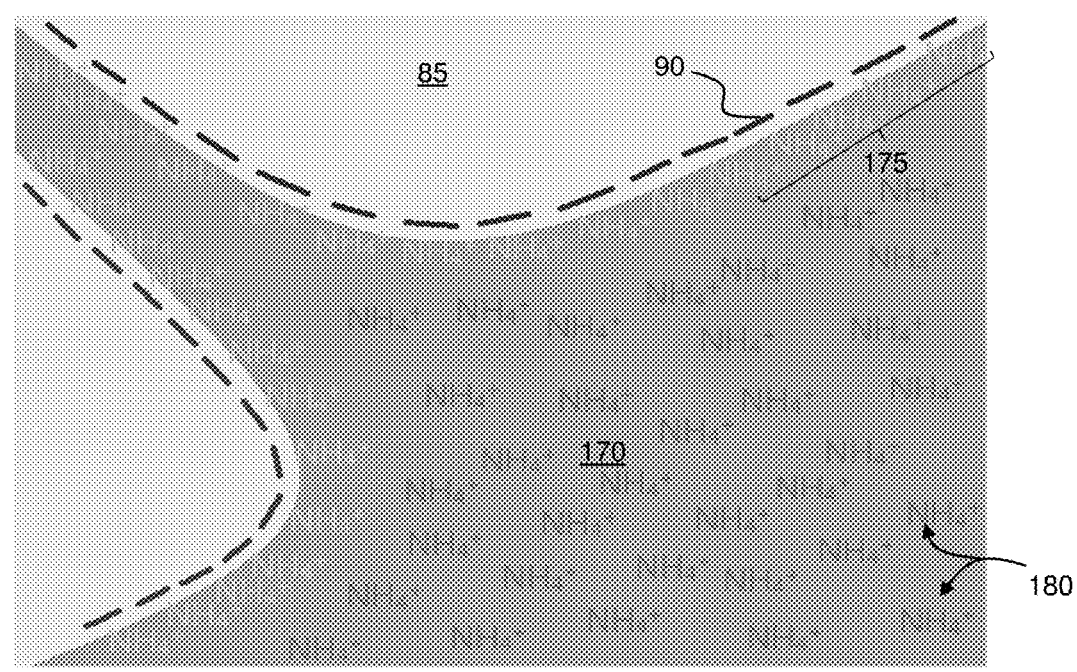

At this stage, the rock sample 80 may be coreflooded in order to remove the "total" exchangeable cations 155 from the sample 80 in order to quantify the total amount of cations adsorbed to exchange sites 90. Such quantification may occur by displacement of the exchangeable cations 155 (as well as organic solvent 165) from the rock sample with a second injection fluid 170, the effect of which is shown in FIG. 5. Injection fluid 170 may include a replacement cation 175, such as $NH_4^+$ adsorbed onto the exchange sites 90. Additionally, injection fluid 170 may also include excess replacement cations 180 that are not adsorbed onto the exchange sites 90, but which are present in the injection fluid 170. To ensure complete displacement of total exchangeable cations 155, the about 50-80 pore volumes of injection fluid 170 may be injected into rock sample 80. In one or more embodiments, the injection fluid 170 may be an ammonium acetate solution, having a concentration ranging from 0.5 to 2.0 M and a pH ranging from 7 to 8.5. It is also envisioned that other injection fluids such as hexaaminecobalt (III) chloride may be used.

From the extract collected from the coreflooding with the injection fluid 170, the amount/concentration of the total exchangeable cations (those cations 155 that are adsorbed to all exchange sites 90, e.g., $Na^+$, $K^+$, $Ca^{2+}$ and $Mg^{2+}$) in the injection fluid extract may be determined by analytical methods, such as but not limited to ion chromatography (IC) specifically cation chromatography, atomic spectroscopic methods such as atomic absorption spectroscopy (AAS), inductively coupled plasma-mass spectrometry (ICP-MS), atomic emission spectrometry (ICP-AES), and optical emission spectrometry (ICP-OES), as well as capillary electrophoresis (CE). In one or more embodiments, the total amount of indigenous exchangeable cations may be considered as a mole equivalent per liter of pore volume and represented as $[NaX]_T$, $[KX]_T$, $[CaX_2]_T$, and $[MgX_2]_T$.

Figure 6:
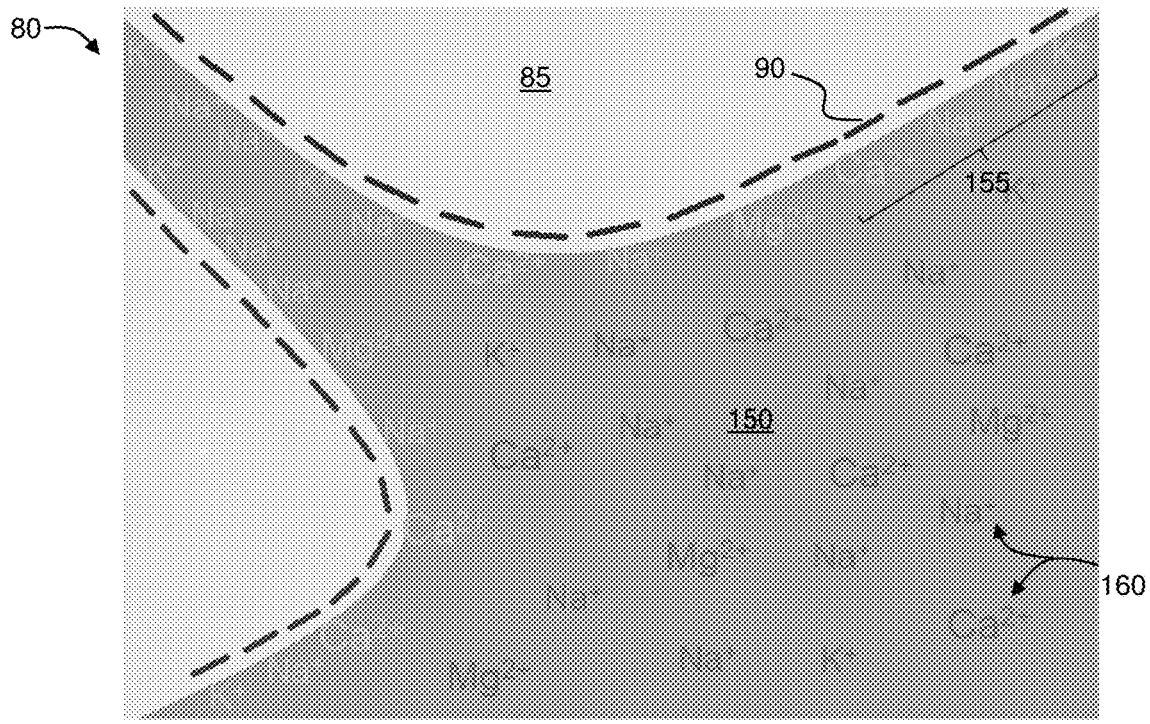

Having determined a total amount of exchangeable cations adsorbed onto exchange sites, the rock core sample 80 may be coreflooded with formation brine to displace the second injection fluid 170, the replacement cation 175, and the excess replacement cations 180 from the rock sample core 80. As shown in FIG. 6, following such displacement, formation brine 150 may be present in the pore spaces between rock particles 85. Formation brine 150 is injected in sufficient volume for complete displacement of the second injection fluid 170, the replacement cation 175, and the excess replacement cations 180 from the rock sample core 80, such that exchangeable cations 155 are adsorbed to all exchange sites 90 present on the surface of rock particles 85 and excess cations 160 in formation brine 150 are also present in the pore spaces between rock particles 85. In order to have complete displacement and equilibrium of the exchange sites 90, a large volume of formation brine 150 may be used, for example, ranging from an estimated 50 to 80 pore volumes. Following the formation brine flooding, the rock core sample 80 may be coreflooded with a reservoir crude oil until reaching irreducible water saturation and equilibrium between formation brine, crude oil, and cation exchange sites 90. In particular, a large volume of reservoir crude oil may be used, such as about 50-80 pore volumes. Reaching such equilibrium, the rock core sample 80, while originally in a non-preserved state, has now been brought into an estimated native state based on the injection of formation brine and reservoir crude oil until reaching irreducible water saturation and equilibrium at the exchange sites 90.

Figure 7:
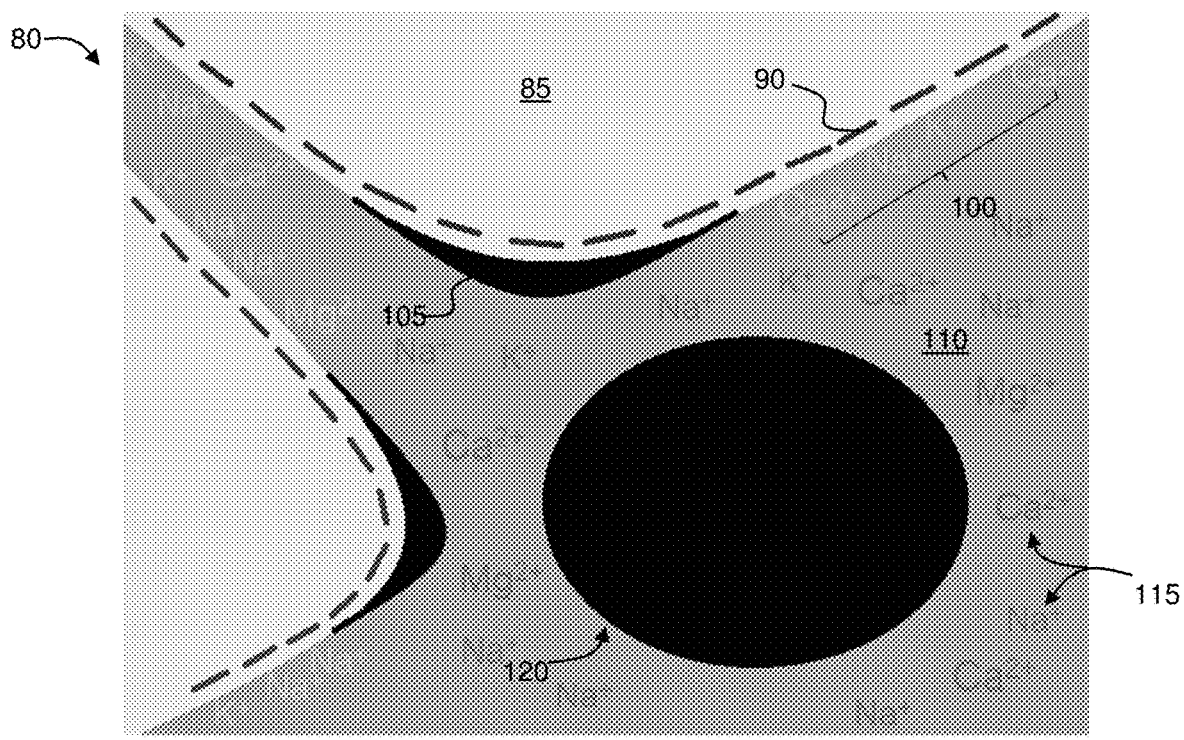

After being brought to an estimated native state, the rock core sample 80 may be coreflooded with formation brine to displace crude oil from the rock core sample. Formation brine may be injected until oil ceases production from the rock core sample. Referring to FIG. 7, FIG. 7 shows a schematic of a rock core sample 80 following the coreflooding with formation brine to displace crude oil. As shown in FIG. 7, rock particles 85 have exchange sites 90 present on the surface thereof. The exchange sites 90 are shown to have some cations 100 and some oil 105 adsorbed thereto. The cations 100 adsorbed onto the exchange sites 90 are referred to as the indigenous exchangeable cations. Otherwise, following the coreflooding with a formation brine 110, the pore spaces between the rock particles 85 are occupied by formation brine 110, including an excess of cations 115 (not adsorbed to exchange sites 90) therein. It is also envisioned that some quantity of residual oil 120 may also be present in the pore spaces between rock particles 85.

Figure 8:
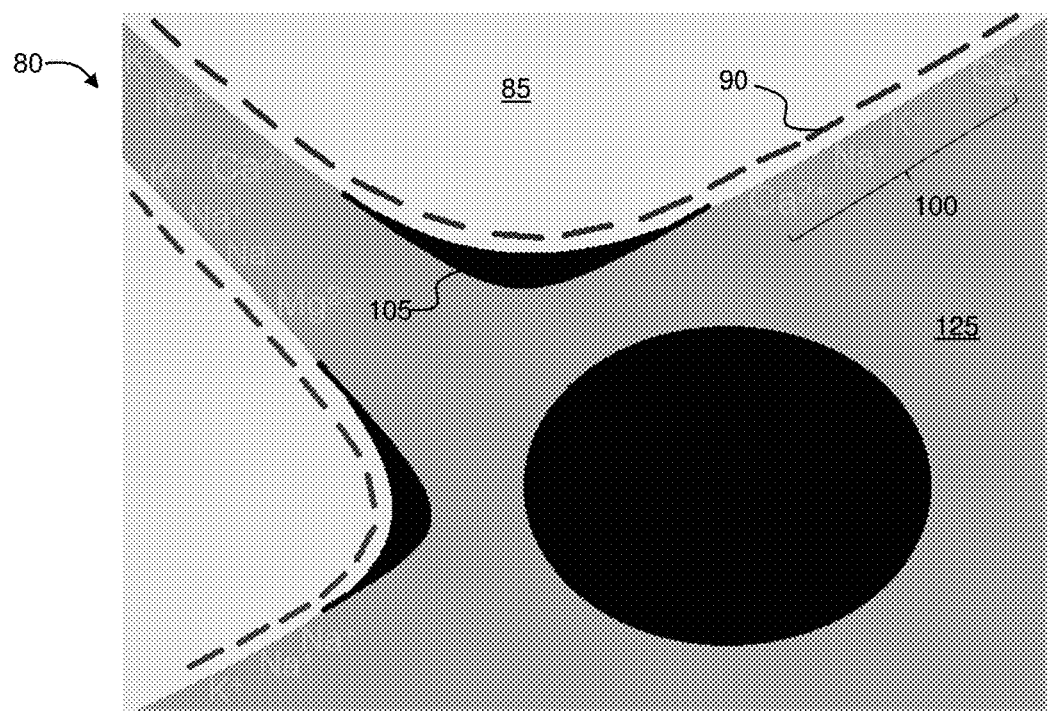

Following the displacement illustrated in FIG. 7, the rock core sample 80 may be coreflooded with an organic solvent, such as but not limited to 95% ethanol, to displace the excess cations 115 (shown in FIG. 7) from the rock core sample 80. To complete the displacement of excess cations 115, a large volume of organic solvent may be used, for example, ranging from an estimated 50 to 80 pore volumes. The effect of such displacement is shown in the schematic illustrated in FIG. 8. As shown in FIG. 8, while the exchange sites 90 still have the cations 100 and oil 105 adsorbed thereto, the pore space between the rock particles 85 is now occupied by organic solvent 125.

Figure 9:
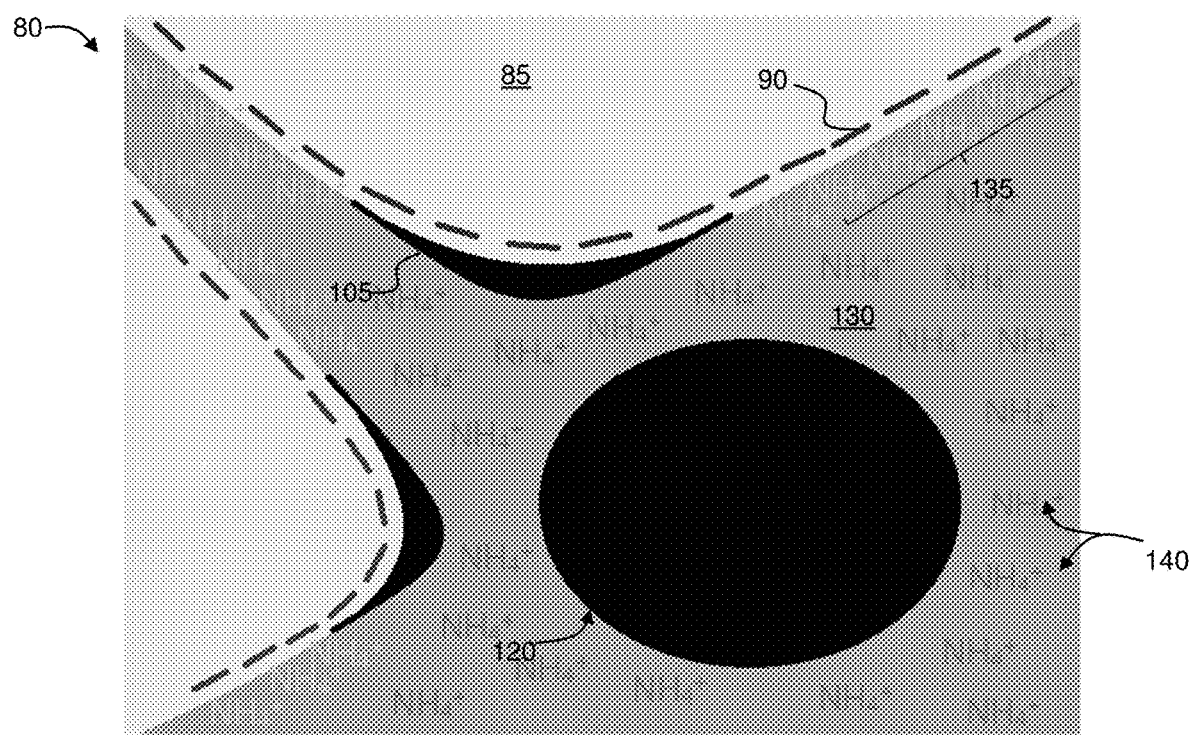

Following the displacement of excess cations, the effect of which is illustrated in FIG. 8, the rock core sample 80 is conducted with an injection fluid to displace the cations 100 (i.e., indigenous exchangeable cations) adsorbed on the exchange sites 90 out of the rock sample 80, the effect of which is illustrated in the schematic shown in FIG. 9. As shown in FIG. 9, following such displacement, in addition to displacing cations (100 in FIG. 8), the organic solvent (125 in FIG. 8) is also displaced from the rock sample 80 such that the pore space between the rock particles 85 is occupied by injection fluid 130 in FIG. 9. Injection fluid 130 may include a replacement cation 135, such as $NH_4^+$ adsorbed onto the exchange sites 90. Additionally, injection fluid 130 may also include excess replacement cations 140 that are not adsorbed onto the exchange sites 90, but which are present in the injection fluid 130. To ensure complete displacement of indigenous exchangeable cations 100, about 50-80 pore volumes of injection fluid 130 may be injected into rock sample 80. In one or more embodiments, the injection fluid 130 may be an ammonium acetate solution, having a concentration ranging from 0.5 to 2.0M and a pH ranging from 7 to 8.5. It is also envisioned that other injection fluids such as a hexaaminecobalt (III) chloride solution may be used.

From the extract collected from the coreflooding with the injection fluid, the amount/concentration of the indigenous exchangeable cations (those cations 100 that were adsorbed to exchange sites 90, e.g., $Na^+$, $K^+$, $Ca^{2+}$ and $Mg^{2+}$ after the rock core sample 80 was brought to an estimated native state) in the injection fluid extract may be determined by analytical methods, such as but not limited to ion chromatography (IC) specifically cation chromatography, atomic spectroscopic methods such as atomic absorption spectroscopy (AAS), inductively coupled plasma-mass spectrometry (ICP-MS), atomic emission spectrometry (ICP-AES), and optical emission spectrometry (ICP-OES), as well as capillary electrophoresis (CE). In one or more embodiments, the amount of indigenous exchangeable cations may be considered as a mole equivalent per liter of pore volume and represented as $[NaX]_e$, $[KX]_e$, $[CaX_2]_e$, and $[MgX_2]_e$.

Depending on whether the wettability of each exchange site and/or the amount of each site occupied by crude oil is to be determined, a series of calculations may be performed using $[NaX]_e$, $[KX]_e$, $[CaX_2]_e$, and $[MgX_2]_e$ and $[NaX]_T$, $[KX]_T$, $[CaX_2]_T$, and $[MgX_2]_T$.

In one or more embodiments, the wettability of $Na^+$, $K^+$, $Ca^{2+}$, and $Mg^{2+}$ exchange sites may be determined. The wettability of each of $Na^+$, $K^+$, $Ca^{2+}$, and $Mg^{2+}$ exchange sites may be represented by $W_{NaX}$, $W_{KX}$, $W_{CaX2}$, and $W_{MgX2}$ and the following equations (1)-(4):

$$W_{NaX} = \frac{[NaX]_T - [NaX]_e}{[NaX]_T} \quad (1)$$

$$W_{KX} = \frac{[KX]_T - [KX]_e}{[KX]_T} \quad (2)$$

$$W_{CaX_2} = \frac{[CaX_2]_T - [CaX_2]_e}{[CaX_2]_T} \quad (3)$$

$$W_{MgX_2} = \frac{[MgX_2]_T - [MgX_2]_e}{[MgX_2]_T} \quad (4)$$

where a value of W=1 means the exchange site is completely oil-wet, and a value of W=0 means the exchange site is completely water-wet. Further, as is apparent, the wettability is calculated for each different exchange site present in the rock core sample.

In one or more embodiments, which of $Na^+$, $K^+$, $Ca^{2+}$, and $Mg^{2+}$ exchange sites are occupied by crude oil may be determined. The amount (in mole equivalent per liter of pore volume) of the $Na^+$, $K^+$, $Ca^{2+}$, and $Mg^{2+}$ exchange sites that are occupied by crude oil may be represented by $[NaX]_O$, $[KX]_O$, $[CaX_2]_O$, and $[MgX_2]_O$ and the following equations (5)-(8):

$$[NaX]_O = [NaX]_T - [NaX]_e \quad (5)$$

$$[KX]_O = [KX]_T - [KX]_e \quad (6)$$

$$[CaX_2]_O = [CaX_2]_T - [CaX_2]_e \quad (7)$$

$$[MgX_2]_O = [MgX_2]_T - [MgX_2]_e \quad (8)$$

Advantageously, the methods of the present application may provide for determinations concerning cation exchange sites in a rock sample, specifically, wettability and/or which are occupied by crude oil, in a manner that differentiates between different cation exchange sites, such as $Na^+$, $K^+$, $Ca^{2+}$, and $Mg^{2+}$. Moreover, such properties may be determined even for a rock core sample that that has not been preserved in reservoir conditions. Using such determinations, an enhanced oil recovery operation may be better designed, for example, in terms of the compositional components included in an EOR injection fluid, whether in water flooding or chemical flooding such as surfactant flooding, polymer flooding, alkaline/surfactant/polymer flooding, or reservoir preflushes for the chemical flooding processes or the like.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed:

1. A method for determining properties of different cation exchange sites in a rock core sample, at a non-preserved state of the rock core sample, the method comprising:
   providing a rock core sample in a non-preserved state;
   displacing all native components out of the rock core sample;
   subjecting the rock core sample clean of native components to a plurality of coreflooding steps to determine a total amount of exchangeable cations adsorbed onto the cation exchange sites when the rock core sample is clean of native components;
   injecting formation brine and then a reservoir crude oil into the rock core sample until reaching irreducible water saturation and equilibrium between formation brine, the reservoir crude oil, and the cation exchange sites, such that the rock core sample includes a plurality of indigenous exchangeable cations adsorbed onto the cation exchange sites, a plurality of cation exchange sites occupied by a crude oil, and one or more fluids occupying pore spaces in the rock core sample;
   subjecting the rock core sample to a plurality of coreflooding steps, the plurality of coreflooding step displacing the plurality of indigenous exchangeable cations, the crude oil, and the one or more fluids in at least two separate coreflooding steps to render the rock core sample clean of the indigenous cations;
   determining an amount of indigenous exchangeable cations adsorbed onto the cation exchange sites; and
   determining at least one property of different cation exchange sites in the rock core sample based on the amount of indigenous exchangeable cations and the total amount of exchangeable cations.

2. The method of claim 1, wherein the subjecting the rock core sample clean of native components to a plurality of coreflooding steps comprises:
   alternately injecting a first organic solvent and a second organic solvent, wherein the second organic solvent is the last injected to render the pore space of the rock core sample clean of native components.

3. The method of claim 2, wherein the subjecting the rock core sample clean of native components to a plurality of coreflooding steps comprises:
   coreflooding the rock sample clean of native components with the formation brine such that the cations present in the formation brine adsorb onto the cation exchange sites and an excess of cations are present in the plurality of interstitial pore spaces of the rock core sample clean of native components;

displacing the excess of cations present in a plurality of interstitial pore spaces of the rock core sample by using a third organic solvent; and displacing the cations adsorbed onto the cation exchange sites of the rock core sample with a first injection fluid until completion of extraction.

4. The method of claim 3, wherein the subjecting the rock core sample to a plurality of coreflooding steps comprises:

displacing the first injection fluid with the formation brine such that the cations present in the formation brine adsorb onto the cation exchange sites;

injecting a reservoir crude oil into the rock core sample until reaching irreducible water saturation and equilibrium between formation brine, the reservoir crude oil, and the cation exchange sites, such that rock core sample includes a plurality of indigenous exchangeable cations adsorbed onto the cation exchange sites, a plurality of cation exchange sites occupied by a crude oil, and one or more fluids occupying pore spaces in the rock core sample;

displacing the crude oil in the rock core sample with a formation brine until oil ceases production;

displacing an excess of cations present in a plurality of interstitial pore spaces of the rock core sample by using a fourth organic solvent; and displacing the plurality of indigenous exchangeable cations from the cation exchange sites of the rock core sample with a second injection fluid until completion of extraction.

5. The method of claim 4, wherein the amount of indigenous exchangeable cations is quantified from an extract of the second injection fluid upon completion of extraction by an analytical method.

6. The method of claim 4, wherein the second injection fluid is an ammonium acetate solution.

7. The method of claim 4, wherein the fourth organic solvent is ethanol.

8. The method of claim 3, wherein the total amount of exchangeable cations is quantified from an extract of the first injection fluid upon completion of extraction by an analytical method.

9. The method of claim 3, wherein the first injection fluid is an ammonium acetate solution.

10. The method of claim 3, wherein the third organic solvent is ethanol.

11. The method of claim 2, wherein the first organic solvent is toluene and the second organic solvent is methanol.

12. The method of claim 1, further comprising: determining a pore volume of the rock core sample.

13. A method for determining an amount of different cation exchange sites occupied by crude oil in a rock core sample, at a non-preserved state of the rock core sample, the method comprising:

providing a rock core sample in a non-preserved state;

displacing all native components out of the pore space of the rock core sample by alternately injecting a first organic solvent and a second organic solvent, wherein the second organic solvent is the last injected;

displacing the second organic solvent with a formation brine to adsorb a plurality of exchangeable cations onto the different cation exchange sites of the rock core sample;

displacing an excess of cations from the formation brine present in a plurality of interstitial pore spaces of the rock core sample by using a third organic solvent;

displacing the plurality of exchangeable cations adsorbed onto the different cation exchange sites of the rock core sample with a first injection fluid until completion of extraction;

displacing the first injection fluid with the formation brine such that the cations present in the formation brine adsorb onto the cation exchange sites;

injecting a reservoir crude oil into the rock core sample until reaching irreducible water saturation and equilibrium between formation brine, the reservoir crude oil, and the cation exchange sites, such that the rock core sample includes a plurality of indigenous exchangeable cations adsorbed onto the cation exchange sites, a plurality of cation exchange sites occupied by a crude oil, and one or more fluids occupying pore spaces in the rock core sample;

displacing the reservoir crude oil in the rock core sample with formation brine until oil ceases production;

displacing an excess of cations present in a plurality of interstitial pore spaces of the rock core sample by using a fourth organic solvent;

displacing the plurality of indigenous cations adsorbed onto the cation exchange sites of the rock core sample with a second injection fluid until completion of extraction;

calculating an amount of indigenous exchangeable cations adsorbed onto the cation exchange sites and a total amount of the exchangeable cations adsorbed onto the cation exchange sites; and calculating the amount of the different cation exchange sites occupied by crude oil based on the amount of indigenous exchangeable cations adsorbed onto the cation exchange sites and the total amount of the exchangeable cations adsorbed onto the cation exchange sites.

14. The method of claim 13, wherein the amount of indigenous exchangeable cations and the total amount of exchangeable cations are quantified from extracts of the first injection fluid and second injection fluid upon completion of extraction by analytical methods.

15. The method of claim 13, further comprising: determining a pore volume of the rock core sample.

16. The method of claim 13, wherein the calculating the amount of different cation exchange sites occupied by crude oil uses equations (5)-(8):

$$[NaX]_O = [NaX]_T - [NaX]_e \qquad (5)$$

$$[KX]_O = [KX]_T - [KX]_e \qquad (6)$$

$$[CaX_2]_O = [CaX_2]_T - [CaX_2]_e, \qquad (7)$$

$$[MgX_2]_O = [MgX_2]_T - [MgX_2]_e, \qquad (8)$$

wherein $[NaX]_O$, $[KX]_O$, $[CaX_2]_O$, and $[MgX_2]_O$ represent $Na^+$, $K^+$, $Ca^{2+}$, and $Mg^{2+}$ exchange sites that are occupied by crude oil; $[NaX]_T$, $[KX]_T$, $[CaX_2]_T$, and $[MgX_2]_T$ represent the total amount of exchangeable cations of $Na^+$, $K^+$, $Ca^{2+}$, and $Mg^{2+}$ adsorbed onto cation exchange sites, and $[NaX]_e$, $[KX]_e$, $[CaX_2]_e$, and $[MgX_2]_e$ represent the amount of indigenous cations of $Na^+$, $K^+$, $Ca^{2+}$, and $Mg^{2+}$ adsorbed onto cation exchange sites.

17. A method for determining a wettability of different cation exchange sites of a rock sample, at a non-preserved state of the rock core sample, the method comprising:

providing a rock core sample in a non-preserved state;
displacing all native components out of the pore space of the rock core sample by alternately injecting a first organic solvent and a second organic solvent, wherein the second organic solvent is the last injected;
displacing the second organic solvent with a formation brine to adsorb a plurality of exchangeable cations onto the different cation exchange sites of the rock core sample;
displacing an excess of cations from the formation brine present in a plurality of interstitial pore spaces of the rock core sample by using a third organic solvent;
displacing the plurality of exchangeable cations adsorbed onto the different cation exchange sites of the rock core sample with a first injection fluid until completion of extraction;
displacing the first injection fluid with the formation brine such that the cations present in the formation brine adsorb onto the cation exchange sites;
injecting a reservoir crude oil into the rock core sample until reaching irreducible water saturation and equilibrium between formation brine, the reservoir crude oil, and the cation exchange sites, such that the rock core sample includes a plurality of indigenous exchangeable cations adsorbed onto the cation exchange sites, a plurality of cation exchange sites occupied by a crude oil, and one or more fluids occupying pore spaces in the rock core sample;
displacing the reservoir crude oil in the rock core sample with formation brine until oil ceases production;
displacing an excess of cations present in a plurality of interstitial pore spaces of the rock core sample by using a fourth organic solvent;
displacing the plurality of indigenous cations adsorbed onto the cation exchange sites of the rock core sample with a second injection fluid until completion of extraction;
calculating an amount of indigenous exchangeable cations adsorbed onto the cation exchange sites and a total amount of the exchangeable cations adsorbed onto the cation exchange sites; and
calculating the wettability of the different cation exchange sites based on the amount of indigenous exchangeable cations adsorbed onto the cation exchange sites and the total amount of the exchangeable cations adsorbed onto the cation exchange sites.

18. The method of claim 17, wherein the amount of indigenous exchangeable cations and the total amount of exchangeable cations are quantified from extracts of the first injection fluid and second injection fluid upon completion of extraction by analytical methods.

19. The method of claim 17, further comprising: determining a pore volume of the rock core sample.

20. The method of claim 17, wherein the calculating the wettability of different cation exchange sites uses equations (1)-(4):

$$W_{NaX} = \frac{[NaX]_T - [NaX]_e}{[NaX]_T} \quad (1)$$

$$W_{KX} = \frac{[KX]_T - [KX]_e}{[KX]_T} \quad (2)$$

$$W_{CaX_2} = \frac{[CaX_2]_T - [CaX_2]_e}{[CaX_2]_T} \quad (3)$$

$$W_{MgX_2} = \frac{[MgX_2]_T - [MgX_2]_e}{[MgX_2]_T} \quad (4)$$

wherein $W_{NaX}$, $W_{KX}$, $W_{CaX_2}$, and $W_{MgX_2}$ represent wettability of $Na^+$, $K^+$, $Ca^{2+}$, and $Mg^{2+}$ exchange sites; $[NaX]_T$, $[KX]_T$, $[CaX_2]_T$, and $[MgX_2]_T$ represent the total amount of exchangeable cations of $Na^+$, $K^+$, $Ca^{2+}$, and $Mg^{2+}$ adsorbed onto cation exchange sites, and $[NaX]_e$, $[KX]_e$, $[CaX_2]_e$, and $[MgX_2]_e$ represent the amount of indigenous cations of $Na^+$, $K^+$, $Ca^{2+}$, and $Mg^{2+}$ adsorbed onto cation exchange sites.

* * * * *